United States Patent [19]

Shaw et al.

[11] Patent Number: 5,084,441
[45] Date of Patent: Jan. 28, 1992

[54] ACETYLATED LOW DENSITY LIPOPROTEINS: A DELIVERY SYSTEM TO PHAGOCYTIC CELLS FOR STIMULATING IMMUNOLOGIC RESPONSE AND HOST RESISTANCE

[76] Inventors: Jack M. Shaw, Alcon Laboratories, 6201 S. Freeway, R2-45, Fort Worth, Tex. 76134; Lawrence B. Schook, 605 N. Hamilton Dr., Champagne, Ill. 61820

[21] Appl. No.: 232,697

[22] Filed: Aug. 16, 1988

Related U.S. Application Data

[63] Continuation-in-part of Ser. No. 21,669, Mar. 4, 1987, abandoned.

[51] Int. Cl.$^5$ .................... C07K 3/00; C07K 13/00; C07K 15/00
[52] U.S. Cl. ........................ 514/2; 530/359; 530/810
[58] Field of Search ............... 514/2; 530/359, 810

[56] References Cited

U.S. PATENT DOCUMENTS 4,466,951 8/1984 Pittman ............................. 530/810

Primary Examiner—Johann Richter
Attorney, Agent, or Firm—Glenna Hendricks

[57] ABSTRACT

Acetylated low density lipoproteins are combined with active and effective lipophilic peptide or other lipophilic immunomodulators, antigens or vaccines to carry the same to macrophage specific targeted receptor mediated endocytosis sites in a living system for treatment of cancer, infection hyperimmune related diseases or deficiencies, or to enhance vaccine induction of immunity. Such receptor mediated endocytosis sites are found on macrophages, monocytes and endothelial cells in organs and tissues of the body.

The combination of acetyl-LDL and a lipophilic peptide or related lipophilic immunomodulators, antigens, polynucleotides or vaccines enables delivery of such to be made across vascular barriers by transcytosis. The penetration of endothelial blood-brain, eye or testicular barriers is included in this concept.

28 Claims, 4 Drawing Sheets

ACETYLATED LOW DENSITY LIPOPROTEINS: A DELIVERY SYSTEM TO PHAGOCYTIC CELLS FOR STIMULATING IMMUNOLOGIC RESPONSE AND HOST RESISTANCE

This is a continuation in part of Ser. No. 021,669 field 3-4-87, now abandoned.

BACKGROUND OF THE INVENTION

1. Field of the Invention

The present invention lies in the field of medicine wherein immunomodulators or vaccines are given for modulation, stimulation, and control of the immune response. 2. The Prior Art What is considered to be the closest prior art consists of liposome-lipophilic muramyl dipeptide analogs and liposome-lymphokines developed for delivery of immunomodulators to macrophages (1-9). A number of papers have described delivery vehicles using intact low density lipoprotein (such as the native unmodified blood, serum or lymphatic lipid particles) as carriers for cytotoxic or therapeutic non-peptide drugs (10-21).

One patent to Pittman, U.S. Pat. No. 4,466,951, Aug. 21, 1984 (22) has suggested using acetyl-LDL to carry covalently bound cellulobiose-therapeutic drug conjugates, however, the chemistry described in this patent for covalently coupling to free amino groups is inappropriate and does not apply to acetyl-LDL since free amino groups have already been acetylated making them unavailable for this purpose.

In contrast to the above, the present invention makes no claims for the covalent coupling of peptide or chemical entities to the acetyl-LDL since that procedure will interfere with the receptor-mediated uptake by macrophages. In both the above Pittman patent (22) and the paper by Nagelkerke, et al., (23) the concept of acetylated-LDL for delivery of immunomodulators, such as lipophilic peptide analogs or vaccines is not contemplated. The blood lipid carrier lipoproteins, such as HDL and LDL chylomicrons have been proposed for vasular site-specific delivery of diagnostic radiopaque agents such as cholesterol iopanoate and polyiodinated 2-substituted triacylglycerols for x-ray organ visualization (24,25,26) with no relation to immune action.

Historically, monoclonal antibodies or other antigens developed for clinical utility have been given systemically as the free antigen or suspended in a non-specific vehicle where they form tissue depots. Alternatively, antigens have been covalently bound or adsorbed to liposomes and synthetic microsphere particles (27-34). The disadvantage of these latter so-called "magic bullet" directed liposomes and microspheres is their large particle size which makes them incapable of penetrating vasular surfaces which restricts their targeted usefulness.

What distinguishes our invention from the prior art is the utilization of the presence of intrinsic cell receptor mediated endocytotic activity as the target for our acetyl-LDL carrier. The acetylated LDL carries lipophilic peptide analogs acting as immunomodulators or vaccines to macrophage processing or reactive sites. The peptides to be carried by acetyl-LDL are modified chemically when necessary to make or enhance their lipid solubility with lipophilic functional groups to render them of sufficient hydrophobicity to partition and anchor in the lipophilic domain of the acetyl-LDL or are already lipophilic. As mentioned previously, this entry of the immunomodulation or vaccine into the acetyl-LDL relates to lipid solubility and is not a direct covalent, coupling to free amino groups on the acetyl-LDL. Other advantages of the acetyl-LDL carrier are its small size (~20 nm), native source and its more natural metabolism that enhances its host compatibility and therapeutic index.

In regard to the action of acetyl-LDL carriers as vaccines or immunoadjuvants previous work has shown that the class II products of the major histocompatibility complex (MHC) involved in immune response are molecules which are cell-surface receptors that bind peptide fragments (of degraded or 'processed' antigens) of foreign and self proteins and present those bound peptides to T lymphocytes (35,36). These class II molecules are capable of binding a large number of peptides of different sequence and are thus general, relatively nonspecific, peptide receptors. The ability to present such peptides to T lymphocytes is a widespread phenomenon depending on macrophages and B cells which express these class II MHC products.

Several groups have now been able to identify those portions of a protein which actually represent the immunogenic portion of the molecules and have shown that these peptide segments are capable of being recognized by the T lymphocytes which generate an immune response (35-38). Morever, it is possible to chemically synthesize such peptides and through the addition of chemical groups or additional amino groups alter the chemical properties of such peptides without affecting their recognition by the immune system (39).

Several factors affect the induction of an immune response by protein vaccines: First, the site of administration (parenterally or orally), the amount of protein administered, and the delivery vehicle (alum or physiologic buffered saline [PBS]. The immunization of humans has required the injection of many low doses of antigen given over a number of years to ensure an efficacious immunization. This latter point may reflect the fact that many self (endogenous) proteins are also being processed which require the immunized peptide to complete for binding to the class II MHC molecule (36,37). The successful use of adjuvants in animal models allows less peptide from having to be injected into the animal. However, such approaches have been limited in human immunizations because of the associated side effects. The application of chemically synthesized peptides to serve as immunogenic compounds currently requires production in large quantities because of the amounts required to effectively immunize clinically.

The use of acetyl-LDL provides a clinical solution to the requirement for large amounts of peptide for the immunization of individuals. The ability to render any immunogenic peptide lipophilic by the addition of hydrophobic residues provides a method for partitioning the peptide into the acetyl-LDL particle. Additionally, many of the peptides which have been studied are actually lipophilic in nature since the areas of a native globular protein which appear to be recognized by the T lymphocytes are amphoteric stretches of 10-15 amino acids which go from hydrophilic to hydrophobic in nature (35,38). Thus, a lipophilic peptide can enter and be partitioned within the acetyl-LDL particle. Because of the properties of this acetyl-LDL lipoprotein particle to selectively bind to macrophages and its inherent adjuvant action, it provides an efficacious carrier of immunogenic peptides. This approach requires only small amounts of peptides and may avoid the need to immunize individuals for more than a single dose.

As discussed, the advantages of acetyl-LDL in our invention are its roles in carrying antigen or macrophage stimulating agents to selectively responding cells of the immune system to enhance their action.

In regard to macrophage action, there is a mutual stimulation between macrophages and immunomodulators such as seen with interferon which produces macrophage stimulation which results in further interferon induction with associated anti-tumor, anti-viral action (40).

A list of references are set out further herein and incorporated in this application for providing a very specific description of all of the prior art known to the inventors.

TYPES OF LIPOPROTEINS AND THEIR CHEMICAL COMPOSITION

Plasma lipoproteins are lipid-protein complexes that are responsible for the transport of water-insoluble lipids in the circulation. Structurally, these complexes consist of an apolar core surrounded by a monlayer coat. Triglycerides and cholesterol esters are the major components of the lipophilic core, while phospholipids, free cholesterol and proteins known as apoproteins are associated with the monolayer surface coat.

On the basis of their physical characteristics and chemical composition, lipoproteins are classified into four major families called chylomicrons (CM), very low density lipoproteins (VLDL), low density lipoproteins (LDL) and high density lipoproteins (HDL). The densities are known at which these various lipoproteins are isolated from the plasma by preparative ultracentrifugation. As the density of these complexes increase, their lipid content and size decrease.

CM and VLDL are the largest and lightest of the lipoproteins and are the major carriers for triglyceride. LDL and classes of HDL, on the other hand, contain esterified and unesterified cholesterol and phospholipid as the predominant lipids. In man, LDL cholesterol contributes about two-thirds of the circulating plasma cholesterol and is primarily transported to tissues as a component of the LDL complex.

ACETYLATED LOW DENSITY LIPOPROTEINS

Acetyl-LDL is prepared by exhaustive acetylation of the apoprotein $\beta$-lysine residues on LDL. The chemically modified low density lipoprotein, acetyl-LDL and other chemical modifications of LDL possess similar targeting advantages as acetyl-LDL. That is, they are selective in their targeting ability to acetyl-LDL receptors on macrophages, monocytes and endothelial cells (41-46). Acetyl-LDL's are unique in that delivery to circulating monocytes and tissue macrophages cannot be selectively achieved by chemically related but unmodified, native LDL. Additional chemical modifications which render the LDL chylomicron lipoproteins capable of binding to the acetyl-LDL receptor include acetoacetylation, maleylation, and succinylation (46). Oxidative treatment of LDL such as that in malondialdehyde modified LDL (46) are also included as a useful procedure which may alter the lysine residues of apoprotein B of LDL. All of these chemical modifications reduce the positive charge of apoprotein B by reaction at the episilon amino groups of lysine. Exhaustive acetylation of the apoprotein B lysine residues renders acetyl-LDL from being further modified by coupling procedures which require available amino groups. This, again, emphasizes the short comings of the Pittman method (22), U.S. Pat. No. 4,466,951, which did not take this into account.

In our invention, acetylated low density lipoprotein (acetyl-LDL) provides a targeted carrier to transport immunomodulators to organs or tissues which harbour macrophages. Acetylated-LDL-lipophilic peptide complexes are targeted to specific preselected receptors found on macrophages or vascular endothelium. The localizing or focussed action of acetylated LDL carriers for receptor mediated entry into macrophages or related phagocytic cells can be used for vaccine enhancement or regulation of immunity and host resistance to modulate resistance to cancer, infection, autoimmune disease, or tissue and organ transplantation.

PRINCIPAL USES OF ACETYL-LDL

Acetyl-LDL containing 50 to 100 molecules of the partition-bound lipophilic peptide analog, muramyl tripeptide phosphatidylethanolamine (a patented immunomodulator of Ciba-Geigy, Basel), is injected systemically or in selected physiological compartments, peritoneal cavity, vascular system, affected organs or tissues for delivery to macrophages, monocytes and mononuclear tissue phagocytic cells. The purpose or use of macrophage activation is to kill tumor cells (such as macrophage-mediated tumor cytotoxicity) and destroy intracellular or cell surface associated parasites, bacteria and viruses (examples, trypanosomes, Leishmania. mycobacteria, Herpes simplex, HSV I and II).

Numerous other small peptide immunomodulators or small peptide-vaccines (such as peptides of normally $</=15$ amino acids) are included as the main concept in this patent application. In addition, it is anticipated that higher molecular weight protein-lymphokines and protein-vaccines can be reduced in size to the smallest "active" peptide and also included as delivery peptides. Similarly, symmetric and asymmetric polynucleotides of small size with interferon or immunoadjuvant inducing capacity are intrinsic to our patent for their immunostimulatory action (47,48).

Essential, however, to the active partition of immunomodulators or vaccine peptides into the lipophilic domain of acetyl-LDL is the requirement of a convalently-bound lipophilic functional group for the immunomodulator. Each peptide immunomodulator or vaccine will, when necessary, be chemically modified with a hydrophobic group (such as ester- or amide-linked fatty acid, cholesterol or phospholipid) much like the muramyl-tripeptide described in this patent which has been modified with the lipophilic phospholipid, phosphatidylethanolamine. The resulting lipophilic peptide analog will be partitioned into the lipophilic domain of acetyl-LDL to form a noncovalent complex. It is anticipated that there may be a few useful peptides, such as cyclosporin, which will require no covalent hydrophobic group since the peptide itself is of sufficient lipophilicity for partitioning into the hydrophobic domain of acetyl-LDL. Another such peptide that can be used with acetyl-LDL is interferon B serine whose high hydrophobicity associates it with plasma lipoproteins (49). Similar lipophilicity and acetyl-LDL carrying capacity wil be found for the interferon inducing, immunostimulating lipoidal amines which are low molecular weight compounds of lipid solubility (44).

Again, covalent coupling of the peptide analog to the acetyl-LDL itself is not included as part of this patent application since no readily available functional group is present on the acetyl-LDL which will allow easy coupling without denaturation or aggregation of the acetyl-LDL with loss of receptor response of macrophages to the acetyl-LDL.

ADVANTAGES OF ACETYL-LDL OVER OTHER PRIOR ART LIPOPROTEINS (1) Acetyl-LDL is ultimately derived from low density lipoprotein which is a natural lipid-containing particle found in the blood of animals. Low density lipoprotein can be isolated in large quantities from human, porcine and bovine sources. Acetylation or other appropriate chemical modification of the apoprotein B lysin residues (such as acetoacetylation, maleylation, succinylation and malondialdehyde treatment) can be performed with uniform results on large batches of lipoprotein (40,43,44).

(2) Acetyl-LDL receptors are specifically found on macrophages, monocytes and endothelial cells which leads to rapid endocytosis of acetyl-LDL and the bound lipophilic peptide or related lipophilic analogs partitioned in the acetyl-LDL which acts as carrier for the lipophilic immune modulator.

(3) It is anticipated that with acetyl-LDL as the carrier, endothelial vascular barriers can be crossed by means of selective acetyl-LDL receptor endocytotic and transcytotic incorporation of the acetyl-LDL-lipophilic peptide or related complexes carried through the phagocytic cell to the basement membrane and from there to interstitial fluid of targeted tissues such as the tumor brain, eye and testes. In this way, macrophages and monocytes in these tissues may be made accessible to the acetyl-LDL-lipophilic peptides or related immunomodulating complexes.

(4) Acetyl-LDL is highly compatible with other components in the blood and will not be as subject to rapid destruction or opsonization and other interactions with blood proteins that interfere with functional integrity such as are seen with liposomes and foreign proteins.

As a lipoprotein, acetyl-LDL are structurally very similar to normal constituents of blood and lymph and the compatibility of acetyl-LDL with blood components should permit prolonged use of acetyl-LDL. This is in contrast to artificially derived lipid-containing particles such as fat, nutritional emulsions or liposomes where thrombophlebitis and hepatic dysfunction, as well as reticuloendothelial (RES) phagocytic clearance and blockade are seen on prolonged administration. Impaired RES function induced by liposomes or nutritional emulsions can predispose to infection, endotoxemic reactions and suppression of the immune response, all of which are avoided in this invention.

(5) Acetyl-LDL is a homogeneous small particle ~20 nm in diameter and no special equipment is necessary to produce this characteristic size. Studies to date with the acetyl-LDL-muramyltripeptide phosphatidylethanolamine complex show no increase in size with this immunostimulator, therefore, it is anticipated that the majority of acetyl-LDL-lipophilic peptide analog complexes will also be of small size. The small ~20 nm size will allow access to a variety of tissues not available to the majority of drug delivery vehicles or liposomal particles currently available or tested in the past. Their small size can relate to their natural endocytic and transcytotic entry into cells, and penetrability through the blood vessel wall.

(6) Acetyl-LDL as a native carrier of macrophage stimulating immunomodulators to targeted macrophages and as a carrier of vaccines or antigens will enhance macrophage processing for long term immunization and for use in antigen desensitization in allergic states. The small size and native origin of acetyl-LDL as a carrier ideally equips it for parenteral, body cavity, and site directed injection for vaccine and immunoadjuvant use.

SOME METHODS OF COMBINING ACETYL-LDL TO MAKE IT EFFECTIVE FOR TREATMENT OF DISEASED AREAS (1) Acetyl-LDL is complexed by partition into lipophilic domains with specific lipophilic peptide antigens, lipophilic immunomodulators or vaccines. The peptide antigen to be used, with the acetyl-LDL carrier, may occur naturally or may require synthesis but in many cases may be derived as an "active peptide" from a larger protein antigen or vaccine. In almost all cases it will be necessary to covalently modify the peptide to render it lipophilic for partition into the hydrophobic domain of the acetyl-LDL carrier. The function of the acetyl-LDL lipophilic peptide analog or related lipophilic immunomodulator complex is to provide specific targeting and enhanced uptake of the peptide antigen, related lipophilic compounds or vaccines by macrophages. The acetyl-LDL carrier provides a targeted receptor oriented vehicle for the above targeted through receptor mediation to organ or tissues for delivery to macrophages, monocytes and mononuclear tissue phagocytic cells.

The acetyl-LDL carrier of immunostimulating agents will have clinical use through targeted macrophage activation. Macrophage activation is necessary for them to kill tumor cells, as seen in macrophage-mediated tumor cytotoxicity, and/or destroy intracellular or cell surface associated parasites: helminths, protozoa, fungi, yeasts, bacteria, viruses and Rickettsia (such as trypanosomes, Leishmania, mycobacteria, Herpes simplex, HSV I and II).

Numerous other small peptide immunomodulators or small peptide-vaccines (such as peptides of normally $</=15$ amino acids) are included as part of the main concept in this patent application. Another example of such are the microbodies of follicular dendritic lymphocytic cells, called iccosomes which enhance immune response. Another example of immunostimulators that can be carried by acetyl-LDL are polynucleotide fragments, such as poly I:C, poly A-U, symmetric or asymmetric which have immunoenhancing effects. Along with polynucleotides, it is anticipated that higher molecular weight protein-lymphokines, interferons, and protein-vaccines can be reduced in size to the smallest "active" peptide or effective particle to be incorporated and delivered by the acetyl-LDL carrier. Also included in the invention of the acetyl-LDL carrier of immunomodulator peptides, are small peptides, lipoidal amines or vaccines which may render the inactivation of an intracellular macrophage/moncyte retrovirus like the HIV I and II and other viruses which reside inside the macrophage. Similar effective immunomodulators can be targeted to chronic intracellular infections against a variety of pathogens provided the tissue possesses an acetyl-LDL receptor.

Essential, however, to the active partition of immunomodulator or vaccine peptide into the lipophilic domain of acetyl-LDL is the requirement that it can have a covalently-bound lipophilic functional group: As discussed previously, each peptide immunomodulator or vaccine, where necessary, will be chemically modified with a hydrophobic group (such as ester- or amide-linked fatty acid, cholesterol or phospholipid) much like the muramyl-tripeptide (MTP) experience which modified the MTP to react with the lipophilic phospholipid, phosphatidylethanolamine (See tables I and II and figures).

Again, covalent coupling of the peptide analog to the acetyl-LDL itself is clearly excluded as a part of this patent application since no readily available functional group is present on the acetyl-LDL which allows for easy coupling. The use of the acetyl-LDL-lipophilic peptide antigen complex is to enhance uptake, processing and presentation of the peptide antigen, lipophilic immunomodulators, or vaccine to macrophages, then to lymphocytes which ultimately will lead to an enhanced immune response. As a necessary factor in immune enhancement, it is anticipated that the lipophilic peptide analog or peptide complex may require enzymatic processing to the free peptide prior to antigen presentation by macrophages to reach effector or responding lymphocytes.

(2) Acetyl-LDL is complexed by partition techniques to lipophilic peptides or other immunomodulators or polynucleotides for delivery to macrophages, monocytes and other mononuclear tissue phagocytic cells for activation or suppression of the macrophage system for treatment of disease states such as cancer, arthritis and those caused by viruses, bacteria, parasites and other pathogens. These macrophage cell types will also be accessible to the acetyl-LDL carrier by endocytotic or transcytotic action across endothelial barriers to such tissues as the brain for the treatment of tumors localized within the brain or central nervous system or for the treatment of virus encephalopathy such as that seen in acquired immune deficiency syndrome ("AIDS") or other viral or pathogenic encephalitides. Where other vascular barriers exist, as in eye, testicle, salivary gland or tumors, the acetyl-LDL will provide a carrier lipoprotein for penetration through the blood vessel into targeted tissue or interstitial space.

OBJECTS OF THE PRESENT INVENTION

It is an object of the present invention to:

Activate macrophages and monocytes in numerous tissue sites for (a) tumoricidal activity in cancer treatment: (b) anti-infectious activity, such as antibacterial, antifungal, antiparasitic and antiviral or rickettsial activity and (c) antigen or vaccine presentation to stimulate the immune response and enhance antibody and host resistance activity to tumors or infection.

A further object is to:

Deliver lipophilic peptide or other lipophilic immunomodulators to macrophages which reside across the blood-brain (central nervous system) and blood-eye barriers. The endothelial affinity and transcytosis of acetyl-LDL would enable lipophilic peptide analog immunomodulators to be delivered to the central nervous system and/or the eye more readily and increase the probability of delivery to macrophages in these sites. Diseases important for this delivery are primary cancer of the brain or cord and "AIDS" related neuropathology caused by HIV-infected mononuclear phagocytic cells.

A further object is to:

Deliver lipophilic peptide analogs or lipophilic immunomodulators across the testicular barrier. In this regard, the testicular microcirculation has a barrier to drug entry that is similar to that seen in the brain and eye. This is particularly seen in acute leukemia where chemotherapy fails to effect entry in testicular tissue and brain to control disease at those sites. Acetyl-LDL may enhance lipophilic peptide analog immunomodulators into macrophages found in cancerous testicular tissue or tissue or tumors with vascular barriers to immunomodulators.

A further object is to:

Enhance lipophilic peptide analog or immunomodulator entry into salivary gland or related glandular tissue. There is evidence that there is a connection between central nervous system drug entry and salivary gland drug concentration suggesting a correlation between blood-brain and blood-salivary gland drug entry.

A further object is to:

Deliver lipophilic peptide analogs directly to the lymphatic system via regional introduction, such as subcutaneous injection for limbs and trunk, head, neck or by intraperitoneal injection. Alternatively, delivery can take place by intra-arterial or direct lymphatic or intraperitoneal or pleural injection or via the thoracic duct to provide immunization or immunomodulation via the lymphatic nodes and liver reticuloendothelial cells and/or pleural and peritoneal space for stimulation of pleural or peritoneal exudate cells.

A further object is to:

Provide a depot preparation for subcutaneous, intra-articular, intramuscular or intraperitoneal lipophilic peptide antigens for immunomodulator administration designed for stimulation or prolongation of immune action and/or providing patient convenience by decreasing the need for repeated injection of antigens or vaccines.

A further object is to:

Use acetyl-LDL to deliver lipophilic peptides or related immunomodulators to sites of inflammation, such as rheumatoid joints to locally inhibit activated macrophages that contribute to inflammation without affecting systemic host resistance governed by other cells involved in host defense.

A further object is to:

Provide a vehicle to deliver lipophilic peptide or related immunomodulators for buccal, nasal or ophthalmic immunologic drug or vaccine administration to regional areas such as liver, spleen, lung, kidney and lymph nodes.

A further object is to:

Provide a vehicle for intravenous, intra-arterial, intralymphatic, intra-peritoneal or pleural, subcutaneous regional and local injection for immunomodulator and vaccine administration for long term vaccine enhancement or for antigen desensitization.

A further object is to:

Provide a vehicle for natural lipid soluble immunomodulators (50) and synthetic lipophilic polynucleotide analogs such as poly I:C, poly A:U, or related structures (47) which have immunostimulating, anti-AIDS (anti-virus) or anti-cancer and interferon inducing capability (47-50) for delivery to macrophages and-/or through barrier sites such as the central nervous system and testicle as described above.

DETAILED DESCRIPTION OF A PREFERRED MODE OF THE INVENTION

Figure 1:
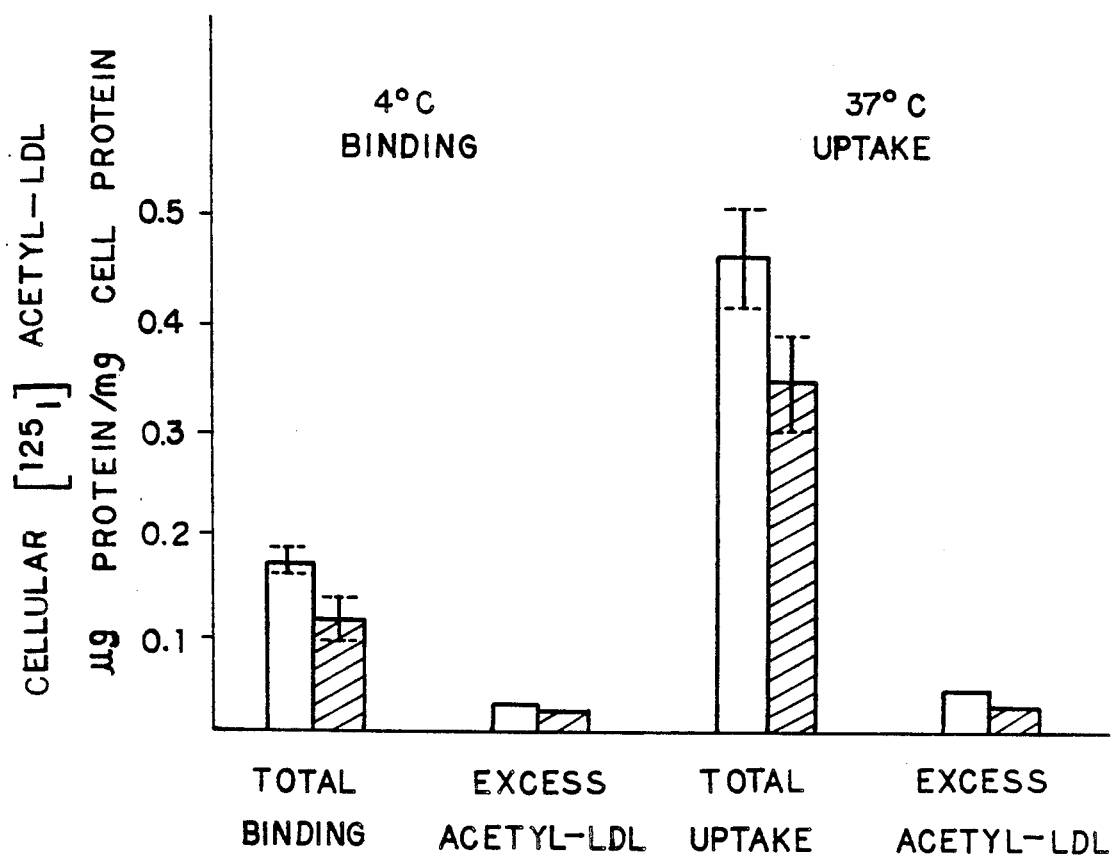

A novel method has been created by the inventors for the selective delivery of lipophilic immunomodulator peptide analogs or lipophilic immunostimulators to stimulate macrophages which results in the induction of anti-tumor activity. The method consists of chemically acetylating native low density lipoproteins to produce an acetylated-low density lipoprotein (acetyl-LDL) and to deliver the lipophilic immunomodulator peptide analog, e.g., muramyl tripeptide phosphatidylethanolamine (MTP-PE), to macrophages via a scavenger lipoprotein-receptor pathway (53,54). Macrophages (monocytes or peritoneal exudate cells) are mononuclear phagocytic cells which protect the body from infection and inhibit tumor growth and induction.

The development of biological response modifiers (BRM) which stimulate host defenses via macrophages to modulate anti-tumor activity has been an area of great interest (55–59). An effective BRM is muramyl dipeptide, a component of the mycobacterium cell wall which is a powerful BRM for inducing anti-tumor activity in the macrophage. This BRM, however, is quickly excreted from the body and has limited usefulness for clinical in vivo regimens because of this (60). To heighten the activity of muramyl dipeptide immunostimulation or macrophage activation, the lipophilic peptide derivative, muramyl tripeptide phosphatidylethanolamine (2) and muramyldipeptide-glyceryl-dipalmitate (9) have been shown to activate macrophages for tumor cell destruction when encapsulated in liposomes. In addition, liposomes containing muramyl tripeptide have been demonstrated to induce protection of mice from fatal herpes simplex type 2 infection in vitro and in vivo (6). However, the non-specificity of liposome-cellular interactions and the inability of most liposome preparations to pass through the blood vessel wall as well as liposomal effects in blocking reticuloendothelial phagocytic function provides little clinical hope for effective liposome use in targeting drugs or BRM's to various organs, tumors and parenchymal cells (61), particularly if macrophage activation is the primary physiologic event desired. The use of acetyl-LDL in our invention is an attempt to circumvent the limitation of liposomal carrier systems for immunostimulatory delivery. Our interest in lipoprotein carriers of lipophilic BRM's such as MTP-PE stems from their being small, naturally occurring plasma particles (20–25 nm in diameter), with an extensive surface and hydrophobic domain. Lipoproteins such as LDL and acetyl-LDL readily pass from the vascular and lymphatic system into the body tissues where they normally play a nutritional role (62,63). Furthermore, it is now possible to sequester a variety of oil soluble drugs, (lipophilic drugs) or vitamins into lipoproteins like LDL or acetyl-LDL (10–13, 15,16). In this regard our laboratory has been the first to partition a lipophilic peptide analog into a lipoprotein for site specific drug delivery. The following data presents the interaction of Acetyl-LDL:MTP-PE complex with macrophages and their activation to an anti-tumor cytostatic state which describes the features of our invention. A major goal of this invention is to utilize the presence of acetyl-LDL receptors on macrophages as a method of specifically enhancing their anti-tumor activity and our data provides evidence for the success of this effort.

SPECIFIC STUDIES

Cytostasis and tumoricidal activities (64), in vitro of thioglycolate-elicited macrophages against two cell lines were examined following incubation with acetyl-LDL:MTP-PE complex. Induction of cytostatic activity in thioglycolate-elicited macrophages toward B16F10 melanoma cells was accomplished by incubations with a minimum of −25 μg acetyl-LDL protein containing 2.5 μg of bound MTP-PE (~40 molecules/particle) (Table 1). The induction of macrophage cytostatic activity by acetyl-LDL:MTP-PE was not affected by liposome bilayers which were also endocytosed by the macrophage. Cytotoxic activity against P815 mastocytoma cells was induced at 40:1 effector: target cell ratios using 18 μg of the acetyl-LDL:MTP-PE protein (Table II).

Interaction of the acetyl-LDL: MTP-PE complex with thioglycolate elicited macrophages was monitored using the fluorescent dye, 1,1-dioctadecyl-tetramethyl carbocyanine (DIL) which remained tightly associated with the lipoprotein immunomodulator complex. The binding and uptake of acetyl-LDL: MTP-PE by macrophages showed specificity in that negligible competition was observed in the presence of excess native LDL or phosphatidylcholine-cholesterol liposomes. The invention is described with reference to Table I, Table II and the drawings FIGS. 1–4) in which: Table I and Table II shows the in vitro cytostatic and cytotoxic action of acetylated LDL: MTP-PE activated macrophages.

FIG. 1: Shows binding and uptake of acetyl-LDL to thioglycolate-elicited macrophages.

Figure 2:
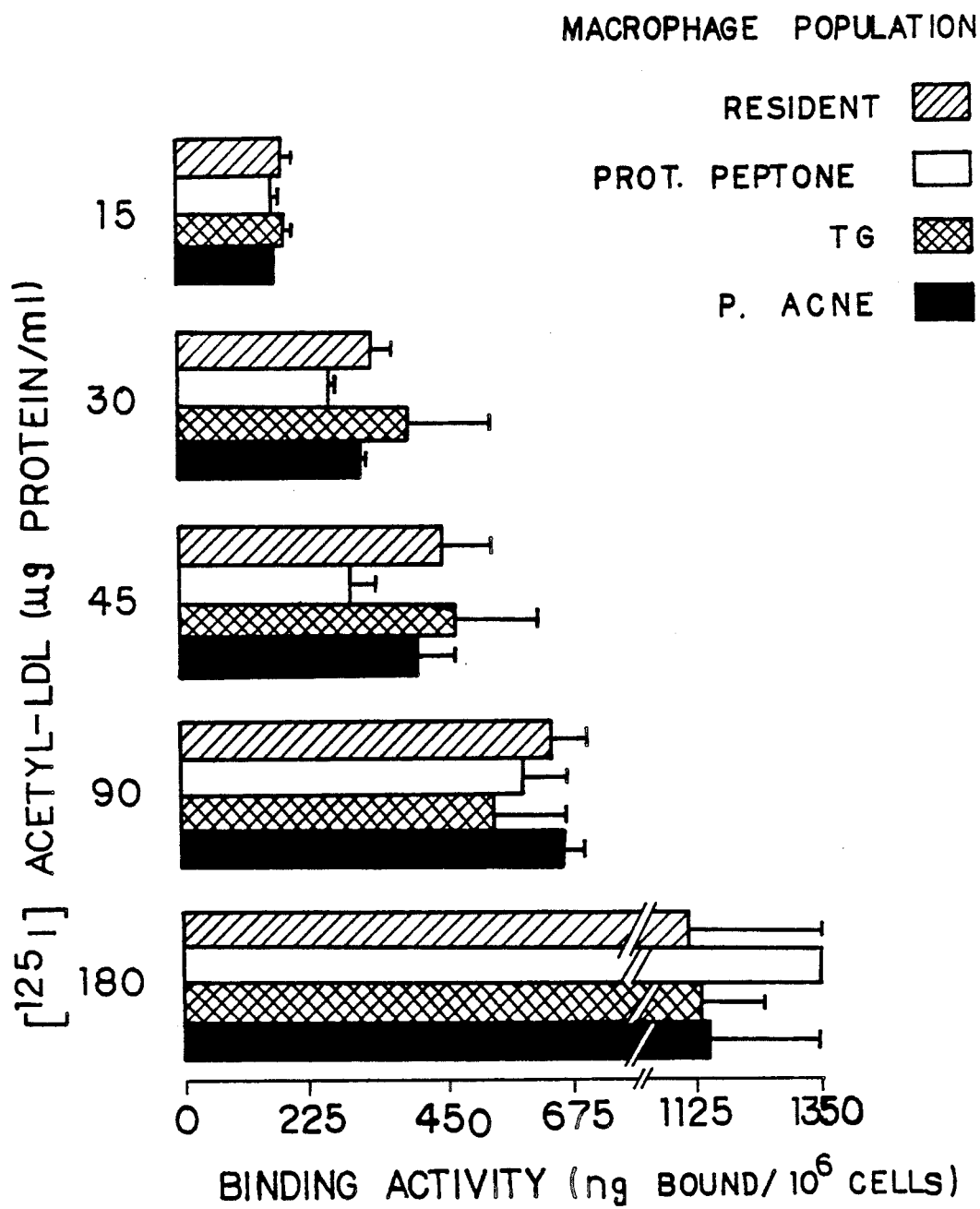

FIG. 2: Shows specificity of acetyl-LDL binding to different cell types.

Figure 3:
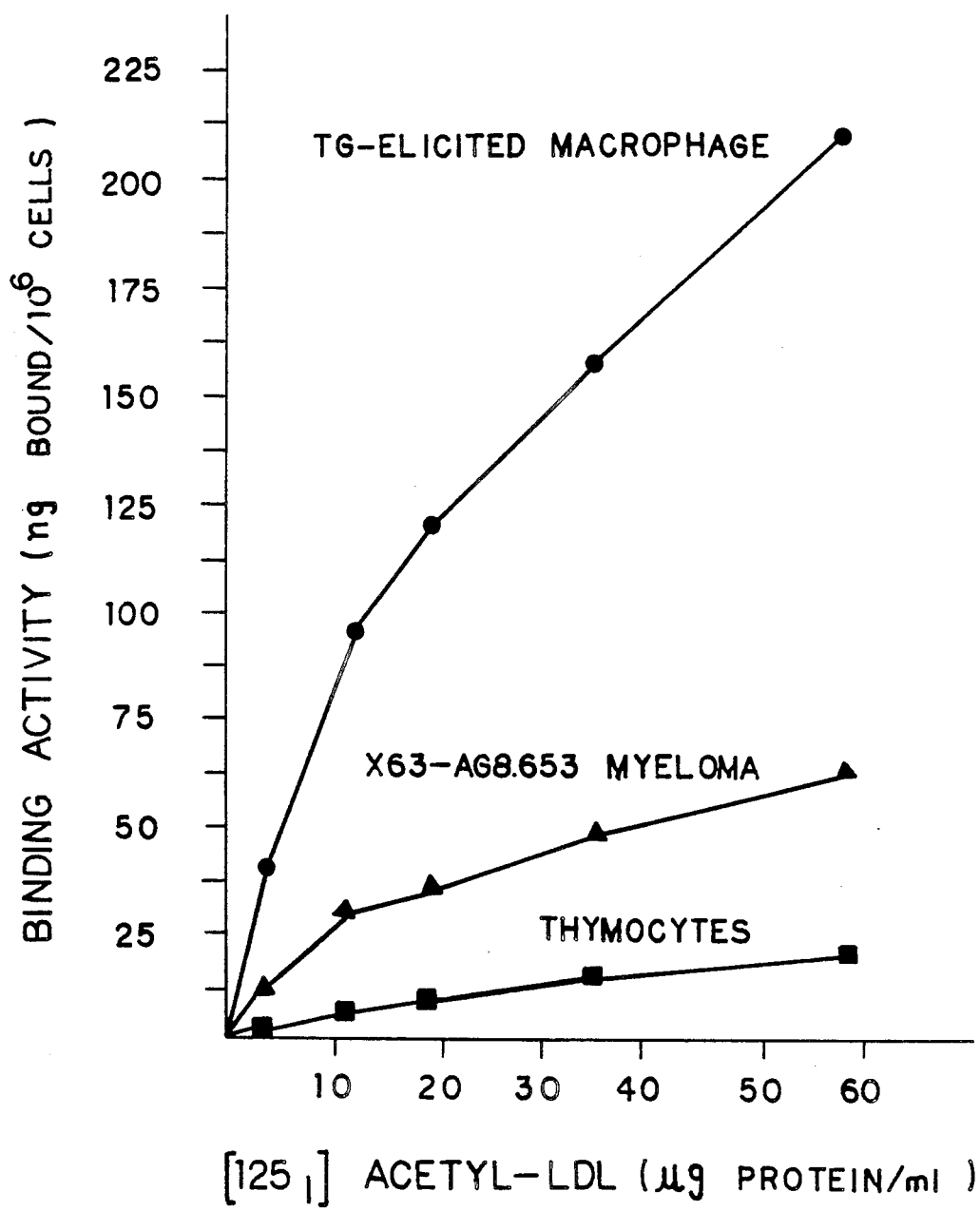

FIG. 3: Shows binding activity of acetyl-LDL by various populations of macrophages activated by different BRM stimulating agents.

Figure 4:
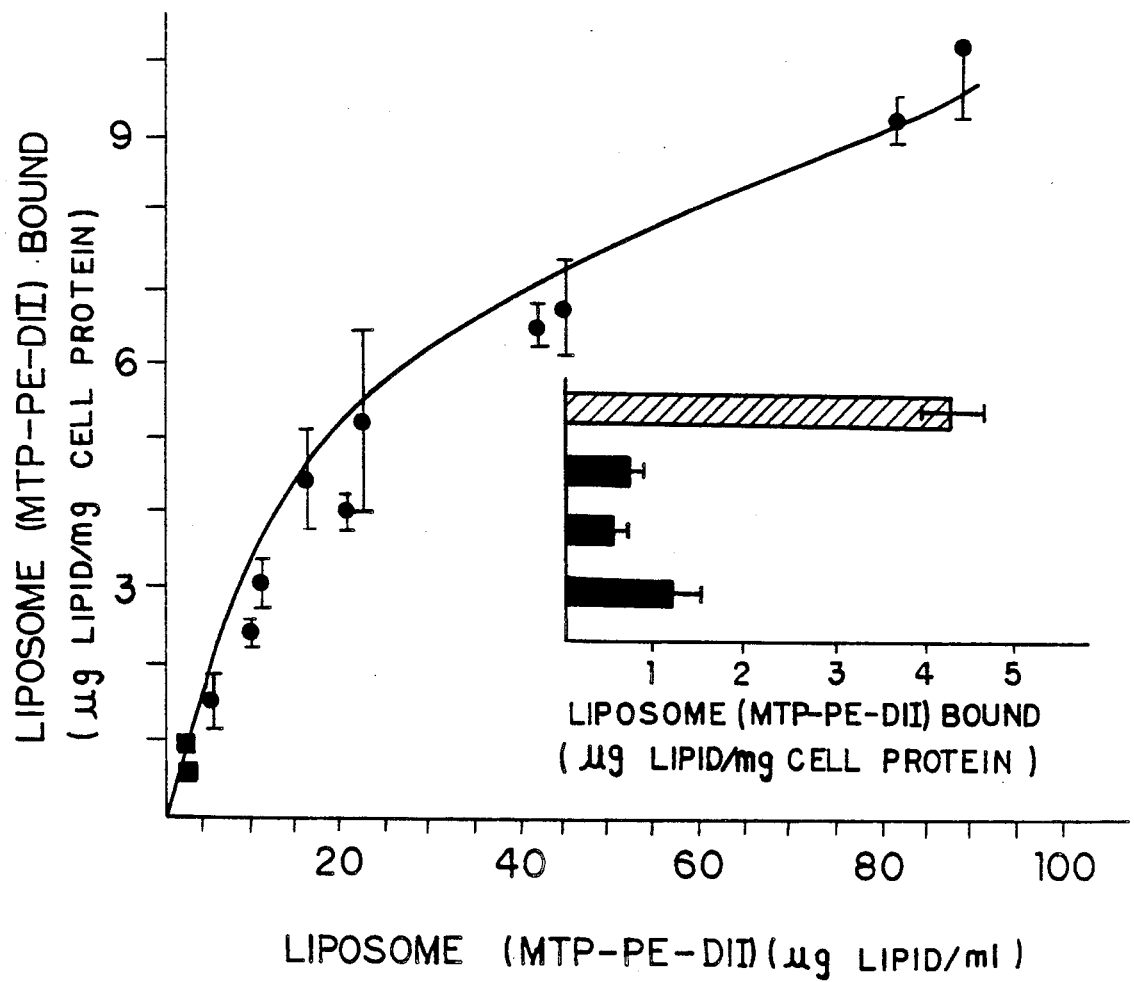

FIG. 4: Shows binding and uptake of acetyl-LDL:MTP-PE-DiI complex by thioglycolate elicited macrophages at 37 degrees.

FIGS. 1–4 show that acetyl-LDL serves as a suitable delivery vehicle to a wide variety of macrophages in different stages of activation (resident, proteose peptone, thioglycolate and propionibacterium, (C. Parvum) elicited macrophages. These studies demonstrate a novel method for the induction of anti-tumor activity in macrophages by use of a chemically modified native serum component, acetyl-LDL, to direct lipophilic immunomodulators such as peptide analogs to tumor sites.

TABLE I

INDUCTION OF CYTOSTATIC ANTI-TUMOR ACTIVITY IN MACROPHAGES BY THE ACETYL-LDL:MTP-PE COMPLEX
B16F10 Melanoma Tumor Target Cells

| Acetyl-LDL (μg protein/ml) | MTP-PE[1] (μg/ml) | % Cytostasis | |
|---|---|---|---|
| | | Acetyl-LDL: MTP-PE Complex[2] | Acetyl-LDL:MTP-PE (Complex + Excess) Liposomes[3] |
| 100 | 0.0 | <5 | ≦5 |
| 100 | 9.9 | 30 ± 11 | 44 ± 5 |
| 50 | 0.0 | <5 | ≦5 |
| 50 | 5.0 | 52 ± 19 | 45 ± 5 |
| 25 | 0.0 | 25 ± 12 | ≦5 |
| 25 | 2.5 | 31 ± 3 | 21 ± 6 |
| 12.5 | 0.0 | <5 | ≦5 |
| 12.5 | 1.3 | 15 ± 8 | ≦5 |
| 6.25 | 0.0 | ≦5 | ≦5 |

TABLE I-continued

INDUCTION OF CYTOSTATIC ANTI-TUMOR ACTIVITY
IN MACROPHAGES BY THE
ACETYL-LDL:MTP-PE COMPLEX
B16F10 Melanoma Tumor Target Cells

| Acetyl-LDL (μg protein/ml) | MTP-PE[1] (μg/ml) | % Cytostasis | |
|---|---|---|---|
| | | Acetyl-LDL: MTP-PE Complex[2] | Acetyl-LDL:MTP-PE (Complex + Excess) Liposomes[3] |
| 6.25 | 0.62 | ≦5 | ≦5 |

[1]Amount of MTP-PE bound to acetyl-LDL (97.2 μg MTP-PE/mg protein) added to thioglycolate-elicited macrophages.
[2]Thioglycolate-elicited macrophages were treated with different concentrations of the complex for 24 hours, unbound complex was washed away and B16F10 melanoma cells were added. After 24 hours, the cultures were pulsed with [3H]thymidine and harvested after 18 hours (effector:target ratio, 10:1).
[3]Addition of Acetyl-LDL:MTP-PE complex in the presence of excess liposomes (1.2 mg lipid/ml) to thioglycolate-elicited macrophages. Liposomes alone induced a cytostatic activity of ±5%.

TABLE 2

In Vitro Activation of Thioglycolate-Elicited
Murine Peritoneal Macrophages for Cytotoxic
Activity of Acetyl-LDL:MTP-PE
P 815 Mastocytoma Target Cells

| Effector to Target Cell Ratio | Percent Cytotoxicity[1] Treatment in vitro | | | |
|---|---|---|---|---|
| | None | Acetyl-LDL: MTP-PE[2] | MTP-PE[3] | Acetyl-LDL[4] |
| 40:1 | 5 ± 2 | 20 ± 8 | 7.5 ± 7 | 3 ± 3 |
| 20:1 | 1.2 ± 2.5 | 12 ± 2.2 | 4.3 ± 1.2 | 6 ± 2 |
| 10:1 | 0.8 ± 2.5 | 14 ± 3 | 8.6 ± 4 | 4 ± 2 |
| 5:1 | 0.5 ± 1 | 3.5 ± 2 | 6 ± 4 | 4.5 ± 4 |
| 1:1 | 0.0 ± 0.6 | 3 ± 3 | 3 ± 4 | 0.5 ± 1 |

[1]Data represents the mean ± S.D. of two separate experiments performed in triplicate.
[2]18.0 ug acetyl-LDL:MTP-PE protein containing 3.6 ug MTP-PE added per microtitre well.
[3]3.6 ug free MTP-PE added per microtitre well.
[4]18.0 ug acetyl-LDL protein added per microtitre well.
The addition of 10 ng lipopolysaccharide had no effect on the cytotoxicity activity (data not shown).

MATERIALS AND METHODS

Isolation and Acetylation of Lipoprotein. Plasma LDL was isolated and purified from fasted, healthy human subjects by differential centrifugation using KBr (12,65). The isolated LDL (density=1.006 g/ml to 1.063 g/ml) was dialyzed to a density of 1.000 g/ml against phosphate buffered saline PBS (5 mM sodium phosphate, 0.15M NaCl, 0.3 mM EDTA) and refloated after 16 hours of centrifugation. The LDL was readjusted to a density of 1.063 g/ml and refloated. The KBr was removed by dialysis against PBS buffer without EDTA and the LDL was passed through a 0.45 μm Millex filter and stored at 4° C.

The purity of the LDL was determined by SDS polyacrylamide gel electrophoresis and revealed no cross contamination between apoprotein A containing lipoproteins or albumin. The LDL (8-10 mg protein) was exhaustively acetylated using acetic anhydride in the presence of sodium acetate on ice as described by Basu et al. (52). The acetylated-LDL was passed through a Sephadex G 15-120 column, dialyzed against PBS buffer, concentrated using an Amicon diaflo cell with a XM-50 filter, and refiltered through a 0.45 μm Millex filter before use.

Iodination of acetyl-LDL was accomplished by the iodine monochloride method of McFarlane (66) as modified by Bilheimer et al (67). The ($^{125}$I) acetyl-LDL was fractionated on a Sephadex G15-120 column, dialyzed against PBS buffer and filtered before use.

Acetyl-LDL:MTP-PE Complex Formation: In a glass tube, methanol solubilized MTP-PE (327 μg) was evaporated to dryness with argon and 2-4 mg acetyl-LDL was added in 2-3 ml of PBS buffer. The mixture was stirred gently with a Teflon-coated stirring bar for 2 hours in the dark at 37°-40° C. under argon. After incubation, the sample was loaded on a 1×10 cm column of Sephadex G15-120 and the acetyl-LDL:MTP-PE complex collected. The complex was passed through a 0.45 μm Millex filter for removal of possible aggregated acetyl-LDL:MTP-PE and for sterilization. The MTP-PE concentration was determined after Bligh and Dyer extraction of the complex (68). MTP-PE was obtained from Ciba-Geigy, Basel.

Macrophages and Cell Types: Adherent, peritoneal macrophages obtained from virus-free female C3H/HeN or C3B6F1 mice (Charles River Breeding Laboratories, Kingston, N.Y.) ages 8-10 wk, were used in all experiments. Macrophages were obtained by reflecting the skin over the abdomen and injecting 5.0 ml of Hank's Balanced Salt Solution (HBSS) (Ca$^{++}$ and Mg$^{++}$ free) into the peritoneal cavity. After agitating the abdomen, cells were drawn off and resuspended in HBSS. Thioglycolate-elicited macrophages were obtained from mice injected intraperitoneally 4 days prior with 1.0 ml of 10% Brewers' thioglycolate. Proteose peptone-elicited macrophages were harvested from mice which had received 1.5 ml of 10% proteose peptone 3 days prior, and *Cornybacterium parvum* (*Propionibacterium acnes*)-elicited macrophages were obtained from animals injected 7 days prior with 1.0 ml volume containing 0.2 mg of the organism. Resident macrophages were obtained from unstimulated animals by saline lavage. The macrophage populations were purified by a two-step wash after 2 hours of adherence. The B16F10 melanoma and the X63-Ag8.653 myeloma and P815 mastocytoma cell lines were maintained in DMEM media supplemented with 10% fetal calf serum (FCS), 2 mM glutamine, penicillin (100 U/ml) and streptomycin (100 μg/ml), 4% sodium bicarbonate, and 15 mM HEPES. Thymocytes were obtained from female C3H/HeN mice (age 8-10 wk).

Macrophage-mediated Cytostasis: Cytostatic activity was determined using a ($^3$H) Thymidine (New England Nuclear Corp) incorporation technique (64). Briefly, 1×10$^5$ thioglycolate-elicited macrophages were incubated in DMEM, 10% FCS with various dilutions of acetyl-LDL:MTP-PE. After 24 hours, the cells were washed twice with warm DMEM and cultured in DMEM (10% FCS), with 1×10$^5$ B16F10 melanoma target cells for 24 hours. The cells were then pulsed for 24 hours with 1 uCi of ($^3$H) thymidine. Cells were harvested using a MASH cell harvester and assayed with a liquid scintillation counter. The results were expressed as a percent inhibition of ($^3$H) thymidine incorporation into the B16F10 target cells (such as % cytostasis).

$$\% \text{ inhibition} = \left(1 - \frac{(CPM\ B16F10\ +\ CPM\ \text{thioglycolate-macrophages})}{CPM\ B16F10\ \text{alone}}\right) \times 100\%$$

Macrophage-mediated cytotoxicity: Cytotoxicity was determined using a [3H] thymidine release assay. Thioglycolate-elicited macrophages were plated in 96-well flat-bottom tissue culture plates (Costar, Cambridge, Mass.) at 4×10$^5$ and 1×10$^4$ macrophage per well. The macrophages were activated by adding 18.0

μg acetyl-LDL:MTP-PE complex protein containing 3.6 μg MTP-PE in 250 μl culture medium at 37 degrees centigrade and 5% $CO_2$. After 24 hours, the plates were washed three times and [3H] thymidine labelled P815 tumor target cells ($1 \times 10^4$) were added to each well. The total assay volume was 250 μl in DMEM with 10% FCS and the plates were incubated an additional 24 hours. After incubation, the microplates were centrifuged for 2 minutes at $250 \times g$ and a 125 μl aliquot of supernatant was removed and counted by liquid spectrophotometry. Total incorporation of radioactivity was determined by adding $1 \times 10^4$ cells to 2 ml of Beckman Redissolve scintillation cocktail.

The percent specific release was calculated.

$$\% \text{ spec. release (such as } \% \text{ cytotoxicity)} = \frac{CPM \text{ Experimental} - CPM \text{ spontaneous release}}{\text{Total } CPM \text{ incorporated into cells}} \times 100\%$$

All samples were plated in triplicate and the data presented as the mean ±S.D. of triplicates.

EXAMPLE 1

Refer to FIG. 1

Binding and Uptake of [$^{125}$I] Acetyl-LDL in Thioglycolate-Elicited Macrophages Thioglycolate-elicited macrophages ($1 \times 10^6$ cells) were placed in plastic wells and allowed to adhere or removed with rubber policeman and allowed to re-adhere. Assays were performed with [$^{125}$I] acetyl-LDL (25 μg protein/ml) by incubation at 4 degrees and at 37 degrees centigrade for two hours. A 40-fold excess of unlabeled acetyl-LDL was used in competion experiments. Following wash steps with PBS-albumin (2 mg/ml) and PBX cells were solubilized in 0.25% SDS in water and counted for radioactivity.

EXAMPLE 2

Refer to FIG. 2

Cell Specificity of [$^{125}$I] Acetyl-LDL Binding

Thiglycolate-elicited macrophages, thymocytes and X63-Ag8.653 myeloma cells were incubated with [$^{125}$I] acetyl-LDL at 4 degrees centigrade in six cell tissue culture plates at $2° \times 10°$ cells/well. After 2 hours, the cells were washed five times, then lysed in 0.05% Triton X-100 and the amount of [$^{125}$I] acetyl-LDL bound was determined.

EXAMPLE 3

Refer to FIG. 3

Radioisotopic Binding [$^{125}$I] Acetyl-LDL to Different Macrophage Species

Binding Activity of [$^{125}$I] Acetyl-LDL by Various Populations of Macrophages The binding specificity of resident, protease peptone, thioglycolate and P. acne (C. parvum)-elicited macrophages for [$^{125}$I] acetyl-LDL was determined. Macrophages were plated in 24 cell tissue culture plates at $1 \times 10(6)$ well at 4 degrees centigrade for 2 hours, then washed five times and lysed in 0.05% Triton X-100. The amount of [$^{125}$I] acetyl-LDL bound was determined. Affinity of acetyl-LDL is seen for all macrophage populations.

EXAMPLE 4

Refer to FIG. 4

Fluorescent Binding and Uptake of Acetyl-LDL:MTP-PE-DiI to Macrophages

Binding and Uptake of Acetyl-LDL:MTP-PE-DiI by Thioglycolate-Elicited Macrophages The binding and uptake of acetyl-LDL:MTP-PE-DiI was carried out at 37 degrees centigrade and the fluorescence intensity of cell-associated DiI recorded. The μg acetyl-LDL:MTP-PE-DiI bound was determined by knowing the quantity of DiI associated with the complex (1.34±0.76 nmol DiI/mg acetyl-LDL protein). The data points represent an average of three separate experiments.

Insert: Uptake of 30 μg of acetyl-LDL:MTP-PE-DiI and in the presence of a 30-fold excess of acetyl-LDL (a) a 30-fold excess of LDL (b) or a 30-fold excess of liposomes (c).

RESULTS

Properties of the Acetyl;LDL MTP-PE Complex

The lipoprotein-immunomodulator peptide analog complex is formed by the partition of the lipophilic MTP-PE from a dried film into acetyl-LDL during a 2 hour incubation at 37°–40° C. Sephadex G15-120 chromatography and filtration of the complex through 0.45 μm filters resulted in 85-90% recovery of the acetyl-LDL protein. Consequently, negligible aggregation of acetyl-LDL during incubation with MTP-PE occurs and the final complex shows no turbidity increase relative to acetyl-LDL. The acetyl-LDL:MTP-PE preparations showed MTP-PE concentrations ranging from 90 to 350 μg MTP-PE/mg acetyl-LDL protein. This corresponds to a value of 36 to 140 molecules MTP-PE/particle of acetyl-LDL. The cholesterol, cholesterol ester and phospholipid composition of acetyl-LDL and acetyl-LDL:MTP-PE agreed within ±15%. The alanine, isoglutamate and ethanolamine components of the chloroform soluble MTP-PE were monitored for appropriate MTP and PE stoichiometry by amino acid analysis after acid hydrolysis. The isoglutamate:alanine:ethanolamine ratio in the chloroform soluble MTP-PE was 1:2:1.

Interaction of ($^{125}$I)Acetyl-LDL with Macrophages (Radioisotopic Proof of Macrophage Localization)

The interaction of ($^{125}$I) acetyl-LDL with macrophages has not been reported for thioglycolate-elicited mouse peritoneal macrophages. FIG. 1 shows the results of ($^{125}$I) acetyl-LDL binding and uptake by macrophages at 4° and 37° respectively. Binding to the cell surface is the predominant interaction of lipoproteins with cells at 4° whereas rapid endocytosis and degradation of the particle occurs as the temperature is increased to 37°. Uptake of ($^{125}$I) acetyl-LDL by macrophages at 37° was approximately threefold higher than binding at 4°. Both sets of temperature experiments showed good competion with a forty-fold excess of unlabeled acetyl-LDL.

The results illustrate that the majority of interaction between lipoprotein and macrophages represents specific binding and uptake. Manipulation of the macrophages by initial attachment to the plastic followed by assay or removal of initially attached cells followed by reattachment, then assay showed comparable binding-uptake response patterns (See FIG. 1).

The overall ($^{125}$I) acetyl-LDL levels bound by macrophages were considerably greater per cell than by the myeloma cell line, X63-Ag8.653 or by mouse thymocytes showing the specificity of acetylated LDL for macrophages. Different populations of macrophages representing distinct stages of activation were also assayed to determine if macrophage populations representing various stages of anti-tumor activation (69) preferentially bound ($^{125}$I) acetyl-LDL. Resident, proteose peptone (responsive), thioglycolate (responsive) and C. Parvum (fully activated)-elicited macrophages all demonstrated similar binding levels of ($^{125}$I) acetyl-LDL (FIG. 3) showing the broad range of specificity for different types of macrophages.

Specific Binding and Uptake of Acetyl-LDL:MTP-PE by Thioglycolate Elicited Macrophages (Fluorescent Dye Binding Proof of Macrophage Localization)

Utilization of iodinated apoproteins in the lipoprotein particles to assess lipoprotein-cellular interactions is complicated by degradation of the iodinated apoprotein (such as acetylated [$^{125}$I] apoprotein B) following endocytosis of the lipoprotein particle. DiI is a lipophilic carbocyanine fluorescent dye which has been used successfully in following the interaction of acetyl-LDL with macrophages and other cell types (42).

The DiI fluorescent dye has two advantages, the first being a one-step technique for determining the total binding-uptake of acetyl-LDL, uncomplicated by degradation steps which occur with iodinated apoproteins. Second, and more important for the present work with MTP-PE, DiI and MTP-PE both have two long acyl chains and represent lipophilic molecules being carried by acetyl-LDL. Consequently, monitoring the binding-uptake of DiI bound to acetyl-LDL is an excellent indicator for the uptake of lipophilic drug species such as MTP-PE.

We have prepared acetyl-LDL MTP-PE DiI complexes by the dry-film stir technique described in the methods section. Interaction of acetyl-LDL:MTP-PE-DiI with macrophages has been determined following assay by extracting and quantitating the DiI using a spectrofluorometer (FIG. 4). The uptake of acetyl-LDL:MTP-PE-DiI complex by macrophages at 37° showed saturation kinetics with maximal binding at a concentration of 160 μg protein/ml. Competition experiments revealed that the uptake of acetyl-LDL:MTP-PE-DiI by macrophages was highly specific for these host defense cells. Unlabeled LDL and synthetic bilayers (liposomes) showed negligible to moderate competition with DiI-labeled acetyl-LDL:MTP-PE complex (FIG. 4 inset) supporting the specific or receptor related binding of acetyl-LDL. Unlabeled acetyl-LDL was an effective competitive inhibitor of acetyl-LDL:MTP-PE-DiI illustrating that the complex was interacting with the macrophage via the acetylated-LDL receptor (FIG. 4 inset).

Functional Activation of Peritoneal Macrophages

Once the uptake efficiency and specificity of the acetyl-LDL:MTP-PE complex was established, we next determined if the complex was capable of inducing tumorostatic activity in macrophage populations. Two different types of macrophage activity were monitored, cytostasis and cytotoxicity.

Table 1 shows that the acetyl-LDL:MTP-PE complex increased the cytostatic activity of thioglycolate-elicited macrophages from C3H/HeN mice following preincubation for 24 hours with acetyl-LDL:MTP-PE. The cytostatic activity of macrophages toward tumor cells was found to correlate with the amount of MTP-PE present in the acetyl-LDL complex. As the concentration of acetyl-LDL:MTP-PE was serially diluted, the induction of cytostatic activity towards the B16F10 melanoma target cells diminished to background levels seen in acetyl-LDL treated control cells. The inclusion of excess liposomes with acetyl-LDL:MTP-PE showed no marked inhibition of the cytostatic activity toward the tumor cell targets (Table 1).

Thioglycolate-elicited macrophages were also treated in vitro with acetyl-LDL:MTP-PE and tested by the more widely used cytotoxicity assay.

Thioglycolate-elicited macrophages from C3B6F1 mice developed cytotoxic activity during treatment in vitro with the acetyl-LDL:MTP-PE complex (Table 2). The acetyl-LDL:MTP-PE treated macrophages became more tumoricidal than cells treated with equal amounts of free MTP-PE or acetyl-LDL alone. After effector to target cell ratios of 40:1, the acetyl-LDL:MTP-PE treated macrophages showed a 2.6 and 6.6 times increase in cytotoxicity during a 24 hour assay as compared to MTP-PE or acetyl-LDL treated macrophages alone. Macrophage effector target ratios less than 10:1 showed no significant differences between acetyl-LDL:MTP-PE treated and control groups.

DISCUSSION

This work indicates that acetyl-LDL:MTP-PE specifically interacts with and delivers an active lipophilic peptide biological response modifier (BRM) to macrophages. Although macrophages possess receptors for the unmodified, naturally occuring LDL, the uptake and degradation of acetyl-LDL occurs at rates approximately twenty-fold greater than LDL (41).

We have found that the partition of MTP-PE into the acetyl-LDL particle does not alter its specificity or binding affinity and that the acetyl-LDL complex interacts with macrophages in all stages of activation. In addition, our results demostrate that binding and uptake of acetyl-LDL was not inhibited by native LDL. Therefore, the acetyl-LDL:MTP-PE/macrophage interactions may not be affected by clinical levels of plasma LDL. However, in vivo compositional alterations of LDL by lipid peroxidation and lipid hydrolysis may generate negatively charged LDL's which might compete for acetyl-LDL binding and endocytosis by macrophages (70).

Of importance to the concept of targeting and specific localization of our invention is that both the acetylation and acetoacetylation-LDL results are not recognized by a variety of non-macrophage cell types like fibroblasts and smooth muscle cells (51, 71). In this regard, we demonstrated that a myeloma cell line (B-lymphocyte) and thymocytes (T-lymphocytes) showed only low levels of binding to acetyl-LDL. In contrast, rat and mouse resident peritoneal macrophages, Kupffer cells, human monocytes, and specific sinusoidal endothelial cells all with phagocytic capacity, express specific receptors for acetylated and acetoacetylated-LDL (41).

A 260,000 dalton acetyl-LDL receptor has also been isolated and characterized from the murine macrophage tumor, P388D1 (72). Macrophages exist normally as heterogeneous populations within the body in various stages of functional activation (73-75). For this reason, it was important to determine which macrophage populations possessed the acetyl-LDL receptor. Under identical experimental conditions, resident, protease peptone, thioglycolate and C. Parvum-elicited macrophages all bound equivalent amounts of acetyl-LDL.

While the specific delivery of lipophilic immunomodulator compounds such as peptide or polynucleotide analogs to non-activated macrophages has obvious therapeutic possibilities, delivery to functionally activated macrophages may also be useful in light of recent findings that gamma-interferon and muramyl dipeptide can act synergistically in enhancing the tumoricidal properties of mouse macrophages (7). It may, therefore, be possible to increase the tumoricidal function of activated macrophages by using acetyl-LDL to deliver multiple activating factors. Alternatively, in the case of chronic inflammatory disease such as rheumatoid arthritis, in which the macrophage is thought to play a role in tissue destruction, the specific targeting of BRM's for regional delivery may allow alteration of macrophage function to modulate the disease without impairing other useful immune functions.

Gilbreath et al (8) have recently reported that exposure of resident macrophages, infected with Leishmania amastigotes, to lymphokine or gamma-interferon activated the cells for microbicidal acitivty. However, lymphokines encapsulated in liposomes, while inducing tumoricidal activity, failed to activate the macrophage for intracellular destruction of the amastigotes. Additonal evidence suggests that although liposomes can be used in cancer thereapy to deliver immunomodulators and render macrophages tumoricidal, they may predispose the patient to serious microbial infection through reticuloendothelial (phagocytic) blockade. In our studies, the addition of liposomes to acetyl-LDL:MTP-PE treated macrophages showed no inhibition for their induced cytostatic activity directed towards B16F10 melanoma cells (Table I). These in vitro findings indicate that the delivery of MTP-PE by Acetyl-LDL offers an original alternative to liposome encapsulated drug delivery.

The acetylated LDL:MTP-PE complex will interact with non-freely migrating macrophage cells such as the sinusoidal endothelial cells of the liver, bone marrow, spleen, and adrenal glands as has been observed for acetoacetylated-LDL (41-43). Therefore, it is reasonable to conclude that receptor-mediated endocytosis or transcytosis of acetyl-LDL:MTP-PE, in vivo will occur on macrophage and endothelial cell types. The desired cellular activity associated with tumoricidal activation by acetyl-LDL:MTP-PE will be highly confined to macrophages. Consequently, the combination of specificity on the part of both the immunoadjuvant or vaccine and its carrier for a particular tissue or cell type provides a useful approach for carrying and targeting immunologic agents and vaccines for the therapeutic management of disease states.

Alternatively, the receptor-mediated endocytosis and transcytosis of acetyl-LDL:MTP-PE in vascular endothelium might provide a focus for macrophage activation in vascular tumors, such as glioblastoma, kaposis, angiosarcoma or tumors with active angiogenesis or for direct action on the atherosclerosis process.

What we claim is:

1. A method of preparing a noncovalently linked complex for targeted delivery to cells having acetyl-LDL (low density lipoprotein receptors comprising the steps of:

(1) modifying a lipoprotein to reduce the positive charge by reaction at the epsilon amion group of lysine residues of apoprotein, and (2) noncovalently complexing the products of step (1) with at least one active agent which either has a lipophilic site or has undergone modification to provide a lipophilic site.

2. A method of claim 1 wherein the modification is accomplished by acetoacetylation, acetylation, maleylation, succinylation, or malondialdehyde treatment.

3. A method of claim 1 wherein the lipoprotein modified in step (1) is a low density lipoprotein.

4. A method of claim 1 wherein the active agent complexed with modified lipoprotein requires no modification.

5. A method of claim 1 wherein the active agent has undergone modification to provide a lipophilic site.

6. A complex comprising at least one active agent noncovalently complexed with a modified lipoprotein wherein the positive charge has been reduced by reaction at the epsilon amino group of lysine residues of the apoprotein.

7. A complex of claim 6 wherein the active agent is muramyl tripeptide phosphatidylethanolamine and the modified lipoprotein is an acetylated LDL.

8. A method of providing a patient with acetyl-LDL receptor cell targeted agent comprising administering an effective amount of a complex of claim 6.

9. A method of claim 8 wherein the complex is administered intravenously.

10. A method of claim 8 wherein the complex is administered into the peritoneal cavity.

11. A method of claim 8 wherein the complex is administered into the intrathecal space.

12. A method of claim 8 wherein the complex is administered into the thoracic duct.

13. A method of claim 8 wherein the complex is administered subcutaneously.

14. A method of claim 8 wherein the complex is administered intradermally.

15. A method of claim 8 wherein the complex is administered by injection into a joint.

16. A method of claim 8 wherein the complex is administered buccally.

17. A method of claim 8 wherein the complex is administered into the pleural cavity.

18. A method of claim 8 wherein the complex is administered intranasally.

19. A method of claim 8 wherein the complex is administered opthalmically.

20. A method of claim 8 wherein the complex is administered into an artery.

21. A complex of claim 6 wherein the active agent is an antigen or vaccine.

22. A complex of claim 6 wherein the active agent is an immunomodulator.

23. A complex of claim 22 wherein the immunomodulator is a leukokine.

24. A complex of claim 22 wherein the immunomodulator is a polynucleotide.

25. A complex of claim 6 wherein the active agent is cyclosporin.

26. A complex of claim 6 wherein the active agent is a lipophilic peptide analog.

27. A complex of claim 26 wherein the active agent is an immunostimulator.

28. A method of claim 1 wherein the active agent complexed with the lipophilic protein produced in step (1) is muramyl tripeptide phosphatidylethanolamine.

* * * * *

UNITED STATES PATENT AND TRADEMARK OFFICE
CERTIFICATE OF CORRECTION

PATENT NO. : 5,084,441
DATED : Jan. 28, 1992
INVENTOR(S) : Shaw, et al.

It is certified that error appears in the above-indentified patent and that said Letters Patent is hereby corrected as shown below:

On the title page, item (76):Inventors, please add:

William Regelson, 1402 Confederate Ave., Richmond, VA 23298

Signed and Sealed this

Thirtieth Day of August, 1994

Attest:

BRUCE LEHMAN

*Attesting Officer*      *Commissioner of Patents and Trademarks*